United States Patent
Sipos et al.

(10) Patent No.: US 9,073,886 B2
(45) Date of Patent: Jul. 7, 2015

(54) PROCESS FOR THE DEPOLYMERIZATION OF A FURANDICARBOXYLATE CONTAINING POLYESTER

(75) Inventors: Laszlo Sipos, Amsterdam (NL); Michael Leroy Olson, Belle Plaine, MN (US)

(73) Assignee: FURANIX TECHNOLOGIES B.V., Amsterdam (NL)

( * ) Notice: Subject to any disclaimer, the term of this patent is extended or adjusted under 35 U.S.C. 154(b) by 191 days.

(21) Appl. No.: 13/976,521

(22) PCT Filed: Dec. 29, 2011

(86) PCT No.: PCT/NL2011/050910
§ 371 (c)(1),
(2), (4) Date: Sep. 5, 2013

(87) PCT Pub. No.: WO2012/091573
PCT Pub. Date: Jul. 5, 2012

(65) Prior Publication Data
US 2013/0345453 A1    Dec. 26, 2013

Related U.S. Application Data

(60) Provisional application No. 61/427,996, filed on Dec. 29, 2010.

(30) Foreign Application Priority Data

Jan. 10, 2011  (NL) ..................................... 2005976

(51) Int. Cl.
*C07D 307/68* (2006.01)
*C08J 11/16* (2006.01)
*C08J 11/24* (2006.01)

(52) U.S. Cl.
CPC ............... *C07D 307/68* (2013.01); *C08J 11/16* (2013.01); *C08J 11/24* (2013.01); *C08J 2367/02* (2013.01)

(58) Field of Classification Search
CPC ...................................................... C07D 307/68
See application file for complete search history.

(56) References Cited

U.S. PATENT DOCUMENTS

2007/0232815 A1  10/2007  Miura et al.
2009/0124763 A1   5/2009  Matsuda et al.
2009/0156841 A1   6/2009  Sanborn et al.

FOREIGN PATENT DOCUMENTS

| EP | 0110629 A1 | 6/1984 |
| EP | 0294863 A1 | 12/1988 |
| EP | 0693527 A1 | 1/1996 |
| EP | 0857714 A1 | 8/1998 |
| GB | 621971 A | 4/1949 |
| JP | 2004250414 A | 9/2004 |
| WO | 2004060987 A2 | 7/2004 |

OTHER PUBLICATIONS

English Machine Translation of JP 2004-250414 A.

*Primary Examiner* — Sun Jae Yoo
(74) *Attorney, Agent, or Firm* — Hoffmann & Baron, LLP

(57) ABSTRACT

A product including a furandicarboxylate compound and diol is obtained from a furandicarboxylate containing polyester in a process, which includes reacting a polymer composition including furandicarboxylate containing polyester with water or an alcohol, such as an alkyl alcohol with from 1 to 12 carbon atoms, in the presence of a base, that is preferably selected from the group consisting of metal hydrides, metal alkoxides, metal carbonates, metal carboxylates, N-heterocyclic carbenes, amidines, guanidines, phosphazenes and mixtures thereof.

17 Claims, No Drawings

PROCESS FOR THE DEPOLYMERIZATION OF A FURANDICARBOXYLATE CONTAINING POLYESTER

CROSS-REFERENCE TO RELATED APPLICATIONS

This application is the National Stage of International Application No. PCT/NL2011/050910, filed Dec. 29, 2011, which claims the benefit of Netherlands Application No. 2005976, filed Jan. 10, 2011, and U.S. Provisional Application No. 61/427,996, filed Dec. 29, 2010, the contents of all of which are incorporated by reference herein.

FIELD OF THE INVENTION

The present invention relates to a process for the depolymerization of a furandicarboxylate-containing polyester.

BACKGROUND OF THE INVENTION

It is known to manufacture polyesters from furandicarboxylic acid or esters thereof and a diol. In this respect reference is made to GB 621971, wherein the preparation of polyesters has been described. In this preparation a glycol is reacted with dicarboxylic acids of which at least one contains a heterocyclic ring. As an example of such a dicarboxylic acid, 2,5-furandicarboxylic acid is mentioned.

EP 294863 describes aromatic polyesters that have liquid crystalline properties. The aromatic polyesters are characterised in that they contain heterocyclic units with two carbonyl groups. The heterocyclic unit may be derived from 2,5-furandicarboxylic acid, 2,4-furandicarboxylic acid, 2,3-furandicarboxylic acid or derivatives of these acids.

In US 2009/0124763 a polymer compound is provided that is the polymerisation product of a furandicarboxylic acid and a diol, and that has a polymerisation degree of 185 to 600. The polymer compound is stated to have excellent mechanical strength. The polymer compound that is exemplified contains 2,5-furandicarboxylate moieties and divalent hydrocarbon groups. Suitable hydrocarbon groups include alkylene groups with 2 to 5 carbon atoms. The polymer thus provided is used as structural material for ink tanks or toner containers or material for copiers, printers or cameras.

A process for the production of furandicarboxylic acids has been described in US 2007/0232815. According to this document furandicarboxylic acid can be prepared by the oxidation of a furan ring compound having two functional groups selected from a hydroxymethyl group, a formyl group and a carboxyl group with a metal permanganate in an alkaline environment. Alternative processes have been discussed in the opening paragraphs of this document. 5-Hydroxymethylfurfural appears to be a suitable starting compound for all processes. 2,5-Furandicarboxylic acid is stated to be a valuable intermediate for pharmaceuticals, agrochemicals, fragrances and so forth.

US 2009/0156841 teaches the production of 5-hydroxymethylfurfural by contacting a carbohydrate source with a solid phase catalyst. Agricultural raw material such as cellulose, starch, sucrose or inulin, can be used as starting material for the production of sugars such as hexoses and pentoses. These sugars are suitable carbohydrate sources for the production of 5-hydroxymethyl furfural. US 2009/0156841 further teaches that a mixture of hydroxymethylfurfural and one or more hydroxymethylfurfural esters may be oxidized to the corresponding furandicarboxylic acid by the addition of an organic acid, cobalt acetate, manganese acetate and sodium bromide under pressure.

From the above state of the art it is evident that furan dicarboxylate containing polyester can be prepared from natural sources. This represents a significant advantage over the production of other polymers that are usually obtained from derivatives of crude oil and other fossil fuels. In order to optimise the environmental friendliness of furan dicarboxylate containing polyester it would be advantageous if such compounds could be re-used. To enable such re-use the present inventors have identified the need to depolymerise furan dicarboxylate containing polyester and to recover the starting materials. This would enable the skilled person to apply the starting materials for any use that would be most advantageous for the skilled person, thus providing a very versatile process.

EP693527 discloses a method for the degradation of unsaturated polyesters using glycol and a catalyst, e.g. an sodium ethanolate. Also in JP 2004 250414 a method is described wherein monomers of polyesters are recovered by solvolysis of the polyester using a monohydric alcohol and a base. WO 2004/060987 discloses a method for the depolymerisation of polyesters and polyamides using a specific carbene catalyst. In an example polyethyleneterephthalate (PET) is depolymerised using 1,3-dimethylimidazole, iodide salt, and potassium tert-butanolate. None of the above references describes that the selection of the polyester results in a difference in depolymerisation behaviour. In EP 857714 the depolymerisation of polyethylene-naphthalenedicarboxylate (PEN) has been described. In this application it is taught that experience in recovering monomers from PET cannot directly be translated to recovery of monomers from PEN.

SUMMARY OF THE INVENTION

It has now surprisingly been found that the depolymerisation of furan dicarboxylate containing polyesters occurs faster than the most common polyester.

Accordingly, the present invention provides a process for the depolymerisation of a furan dicarboxylate containing polyester, which process comprises reacting the furandicarboxylate containing polyester with an alcohol or water in the presence of a depolymerisation catalyst to yield a product comprising a furandicarboxylate compound and diol. By furandicarboxylate compound is understood the furandicarboxylic acid and any other compound that contains the furandicarboxylate group, in particular the mono- or diester of furandicarboxylic acid or a salt of furandicarboxylic acid.

DETAILED DESCRIPTION OF THE INVENTION

The versatility of the present invention is shown by the situation that by applying the present invention the skilled person is enabled to use, e.g., the ink tanks of US 2009/0124763 in the process of the present invention and turn them into the valuable pharmaceutical intermediates of US 2007/0232815.

The furandicarboxylate containing polyester may contain several isomers of furandicarboxylate moieties. In this context it is possible to have polymers comprising units of 2,3-furandicarboxylate, 2,4-furandicarboxylate, 3,4-furandicarboxylate and 2,5-furandicarboxylate and mixtures thereof. However, mechanical strength has been shown to be a significant property of the polymers that have 2,5-furandicarboxylate moieties. Accordingly, the polymer composition of the present invention preferably comprises 2,5-furandicarboxylate containing polyester.

In addition to furandicarboxylate moieties, the polyester may comprise one or more other diacid or alpha/omega hydroxycarboxylic acid residues. Examples of other diacids include phthalic, isophthalic, terephthalic acid and alpha/omega alkylene-dicarboxylic acids, having from 2 to 10 carbon atoms. Examples of hydroxycarboxylic acids include lactic acid, citric acid, 3-hydroxypropionic acid, 3-hydroxy-2-methylpropionic acid, 3-hydroxybutanoic acid, 3-hydroxy-2-methylbutanoic acid, 3-hydroxy-2-methylpentanoic acid, 3-hydroxy-3-methylbutanoic acid, 2,3-dimethyl-3-hydroxybutanoic acid and 3-hydroxy-3-phenylpropionic acid.

The furandicarboxylate containing polyesters comprise moieties that result in a diol after depolymerisation. The furandicarboxylate polyesters may further comprise other moieties with at least two functional groups. The functional groups are suitably selected from amino, thiol and hydroxyl groups. Suitably these functional groups form part of monomers that also comprise alkylene groups. Preferably, the polyester is constituted by furandicarboxylate units and residues of diols. These diols may comprise di- or trialkylene glycol groups such as diethylene glycol, triethylene glycol, dipropylene glycol or tripropylene glycol. The preferred diols are alkylene diols. As has been described in the prior art, the alkylene group in the furandicarboxylate containing polyester may be selected from a variety of alkylene groups. So, preferably, the polyester comprises poly(alkylene 2,5-furandicarboxylate). Suitably, the alkylene groups, in particular those in the poly(alkylene 2,5-furandicarboxylate), comprise from 2 to 6 carbon atoms. Such groups include linear moieties such as hexamethylene, pentamethylene, tetramethylene, trimethylene and ethylene. Also branched alkylene groups may be used, such as 1,2-propylene, iso-butylene, s-butylene, isopentylene and neopentylene. Advantageously, the alkylene group is selected from linear hydrocarbyl groups having 2 to 4 carbon atoms.

The molecular weight of furandicarboxylate containing polyester that can be subjected to the depolymerisation of the present invention is not critical. The polymer may be selected from oligomers to high molecular weight polyesters. US 2009/0124763 discloses poly(alkylene furan dicarboxylate) having a polymerisation degree of 185 to 600, corresponding to number average molecular weights that theoretically may vary from about 33,000 to 135,000. Such polyesters can suitably be depolymerised in the present process.

As indicated above, the polymer composition that is used in the present process can be any composition that contains the furandicarboxylate containing polyester. Advantageously, the polymer composition has been obtained from polyester waste. The waste can be from any source, including the applications of electric and electronic components and the like, as described in US 2009/0124763. Especially in the case of waste, the furandicarboxylate containing polyester may suitably be part of a polymer composition further comprising one or more polymers selected from the group consisting of polyethylene-terephthalate, polyolefins, polyvinylchloride, polylactic acid, polyamides and mixtures thereof.

Dependent on the desired use of the product of the depolymerization, the skilled person may select water or an alcohol. Suitably the alcohol is selected from those alcohols that comprise from 1 to 12 carbon atoms. Since the depolymerization runs most smoothly with the use of the lower alcohols, i.e. alcohols having from 1 to 4 carbon atoms, the more preferred alkyl alcohols are methanol, ethanol, ethylene glycol, 1,3-propane diol, 1,4-butadiol or mixtures thereof. In some instances it is advantageous to depolymerise the furandicarboxylate containing polyester first in the presence of a diol, such as ethylene glycol, and to transesterify the product thus obtained with a different alcohol, suitably a monoalcohol such as methanol or ethanol.

The state of the art has disclosed a large number of depolymerisation catalysts. Such catalysts include acidic catalysts, such as mineral acids, e.g. hydrochloric acid, sulphuric acid and phosphoric acid. Other suitable acids include sulphonic acids, such as methane sulphonic acid or p-toluene sulphonic acid, and carboxylic acids, e.g. those having from 2 to 20 carbon atoms. It is also possible to use various metal compounds as depolymerisation catalyst. The metal of these compounds can be selected from a wide range, including the alkaline earth metals, manganese, zinc, titanium and other transition metals. The anionic moiety of the compounds is not critical and may include carboxylate, such as acetate, halide, such as chloride, carbonate and sulphate. Preferably, the catalyst comprises a base. Advantageously, the catalyst is homogeneous. The catalyst can be any homogeneous basic catalyst known to those skilled in the art. Suitably, the homogeneous catalyst is selected from the group consisting of metal alkoxides, metal hydroxides, metal carbonates, metal carboxylates and mixtures thereof. The metal is such group is suitably selected from the alkali metals, in particular sodium and potassium. When as product of the depolymerisation an ester is envisaged and the depolymerisation takes place in an alcohol, the metal alkoxide is preferably derived from the same alcohol as the alcohol in which the depolymerization takes place. For example, if the reactant alcohol is methanol then the catalyst might be a metal methoxide such as sodium or potassium methoxide.

Other suitable organic basic depolymerisation catalysts may be chosen from other saponification or transesterification catalysts including N-heterocyclic carbenes, such as triazol-5-ylidenes or 1,3-disubstituted imidazol-2-ylidene as disclosed in, e.g. J. Chem. Educ., 87 (2010) 519-521 and Organic Lett., 4 (2002) 3587-3590, amidines, such as those disclosed in EP 110 629, guanidines, such as di- or triphenylguanidine, guanidine carbonate or tetramethylguanidine and 1,5,7-triazabicyclo[4.4.0]dec-5-ene (TBD), and phosphazenes. Phosphazenes are a class of chemical compounds in which a phosphorus atom is covalently linked to a nitrogen atom by a double bond. Phosphazenes are also known as iminophosphoranes and phosphine imides. Phosphazene bases are strong non-metallic non-ionic and low-nucleophilic bases. The catalysts N-heterocyclic carbenes, amidines, guanidines and phosphazenes can also be used in mixtures containing two or more of these catalysts and in mixtures with the metal-containing catalysts described above. The temperature of the present process can be moderate. Preferred catalysts include alkali metal alkoxides, wherein the alkoxides contain from 1 to 4 carbon atoms, and guanidines, in particular 1,5,7-triazabicyclo[4.4.0]dec-5-ene (TBD).

The skilled person may choose the temperature within wide ranges. Typically, the temperature ranges from room temperature, e.g., 18° C., to 350° C. The pressure of the reaction can also be selected in accordance with the desires of the skilled person. The length of reaction will depend on the choice of alcohol and on the choice of reaction temperature. The pressure can be chosen as such to accommodate the chosen alcohol and temperature. Therefore, the reaction pressure may range from 0.5 to 200 bar, preferably from 1 to 10 bar.

The process according to the present invention is suitably preceded by dispersing at least part of the polyester in an alcohol or water to yield a polyester slurry. This results is finely divided polyester particles whereby the depolymerisation is facilitated. By heating the dispersion a homogeneous phase may be obtained.

The depolymerisation according to the present invention is suitably carried out in an excess of water and/or alcohol. This facilitates that any equilibrium reaction is shifted towards the depolymerisation. Therefore, the weight ratio of furandicarboxylate containing polymer to water or alcohol is suitably from 1:1 to 1:100, preferably from 1:2 to 1:25. The amount of base is not critical. Good results are attainable with quantities of base that range from 0.5 to 25% wt, preferably from 1 to 10% wt, based on the weight of the water and alcohol.

The reaction may be performed in a batch manner. In such a case the reactants, i.e., the polymer composition, the base and the alcohol and/or water, are combined in a vessel, optionally a pressure vessel like an autoclave, and the reaction conditions are applied. It will be clear that it would be advantageous from a commercial standpoint to perform the present process in a continuous manner. In a continuous process a stream containing the polymer composition is continuously fed into a reactor and a product stream containing furan dicarboxylate and diol, and optionally other depolymerisation products, are continuously withdrawn from the reactor. In addition to the polymer composition, also the base and the alcohol or water are continuously fed into the reactor. Suitable continuous reactors include a plug flow reactor and a tank reactor. Since the duration of the reaction will take some time, typically at least 1 hr, the process is preferably conducted in a continuous stirred tank reactor. The furan dicarboxylate compound is preferably separated from the product stream. Also other components may be separated from the product stream. As stated above, the depolymerisation products also comprise a diol. It is advantageous to also recover the diol from the product stream. The recovery of furandicarboxylate and diol may be easily effected by means of conventional separation techniques, such as precipitation and filtration or distillation. Optionally, the recovered products may be subjected to further purification. When water and a base are used, free dicarboxylic acid is suitably obtained after treatment of the recovered product with a Brønsted acid. Evidently, the selection of the Brønsted acid is not critical. The acid may be a mineral acid, such as hydrochloric, sulphuric or nitric acid, but it may also be an organic acid, such as a carboxylic acid, e.g. acetic acid or formic acid, or an alkane sulphonic acid, e.g., methane sulphonic acid, or an arene sulphonic acid, e.g., p-toluene sulphonic acid.

The furandicarboxylate that is recovered from the product stream may be used for various objectives, including for use as fuel or fuel additive. Since the alkyl esters of furandicarboxylic acid are excellently suited for use in the manufacture of furan dicarboxylate containing polyesters, at least part of the furan dicarboxylate that has been separated from the product stream is suitably used for the manufacture of furandicarboxylate containing polyesters. However, as already indicated above, the starting materials that have been recovered can be utilised for any purpose.

The invention will be further illustrated by means of the following examples.

EXAMPLE 1

Into a 10 mL vial equipped with a magnetic stir bar the following materials were placed: 0.50 g poly(butylene 2,5-furandicarboxylate) (PBF) (particle size 0.6-1.4 mm, number average molecular weight $M_n$=17900), 5.0 mL methanol and 0.067 mL 25 wt % solution of sodium methoxide (c(final) =0.058 mol/L). The vial was placed to a 90° C. oil bath and stirring was started. The polymer dissolved completely within 30 minutes. The reaction mixture was left in the bath for another 90 minutes. The solution was transparent though slightly yellow. It was cooled down to ambient temperature and dimethyl 2,5-furandicarboxylate (DMF) crystallized out. The crystals were filtered and dried in a vacuum desiccator. The process yielded 265.6 mg dimethyl 2,5-furandicarboxylate (60.6%). When some methanol was evaporated from the solution, more DMF crystallised out. This indicates that the yield is determined by the solubility of DMF.

EXAMPLE 2

Into a 10 mL vial equipped with a magnetic stir bar 1.00 g poly(ethylene 2,5-furandicarboxylate) (PEF) ($M_n$=15,100, particle size of 0.6-1.4 mm) and 5 mL 2.5 M sodium hydroxide solution were placed. The vial was closed and heated at 100° C. for six hours under stirring. After that, the solution was cooled down to room temperature, filtered and diluted with 5 mL water. The diluted solution was then acidified under stirring with 2.5 M hydrochloric acid solution until pH 2. The precipitated white 2,5-furandicarboxylic acid was filtered, washed with water and dried in vacuum at ambient temperature overnight. The yield was 710.5 mg (82.9%).

EXAMPLE 3

Into a 10 mL vial equipped with a magnetic stir bar the following materials were placed: 0.50 g PEF (d<0.2 mm, $M_n$=16,200), 5.0 mL methanol and 40.1 mg 1,5,7-triazabicyclo[4.4.0]dec-5-ene (TBD) (c(final)=0.058 mol/L). The vial was placed to a 90° C. oil bath and stirring was started. The polymer dissolved completely within 4 minutes. The reaction mixture was left in the bath for another 30 minutes. The solution was transparent though slightly yellow. It was cooled down to ambient temperature when dimethyl 2,5-furandicarboxylate (DMF) crystallized out. The crystals were filtered and dried in a vacuum desiccator. The process yielded 318.0 mg dimethyl 2,5-furandicarboxylate (63.1%).

EXAMPLE 5

Comparison of Methanolysis Rate of PET and PEF

Tensile bars were made from PET, poly(ethyleneterephthalate) ($M_n$ 16,800), and PEF ($M_n$ 16,200) with exactly the same dimension of 10×52×1 mm. The bars were placed separately into 13 mL methanol solution of sodium methoxide (c=0.044 mol/L) and the two vials were heated in the same oil bath at 90° C.

After a given time, the vials were transferred into an ice bath, the bars dried and weighed. The results are shown in Table 1.

TABLE 1

|  | Weight (mg) | |
| --- | --- | --- |
| Time (min) | PET | PEF |
| 0 | 768.1 | 787.6 |
| 30 | 765.1 | 607.9 |
| 60 | 758.9 | 474.8 |
| 75 | 755.1 | 419.7 |
| 90 | 751.5 | 379.7 |

Table 1 shows that the PEF bar dissolves much faster than the PET bar, indicating that the methanolysis rate is much faster for PEF than for PET.

The invention claimed is:

1. A process for the depolymerization of a furandicarboxylate containing polyester, which process comprises reacting the polyester with an alcohol or water in the presence of a depolymerisation catalyst to yield a product comprising a furandicarboxylate compound and diol.

2. The process according to claim 1, wherein the polyester comprises poly(alkylene 2,5-furandicarboxylate).

3. The process according to claim 2, wherein the alkylene moiety of the poly(alkylene 2,5-furandicarboxylate) comprises 2 to 6 carbon atoms.

4. The process according to claim 1, wherein the depolymerisation catalyst comprises an acid catalyst, a metal compound or a base.

5. The process according to claim 4, wherein the depolymerisation catalyst comprises a base.

6. The process according to claim 5, wherein the base is selected from the group consisting of metal alkoxides, metal hydroxides, metal carbonates, metal carboxylates, N-heterocyclic carbenes, amidines, guanidines, phosphazenes and mixtures thereof.

7. The process according to claim 1, which is preceded by dispersing at least part of the polyester in an alcohol or water to yield a polyester slurry.

8. The process according to claim 1, when water and a base are used, free dicarboxylic acid is obtained after treatment with a Brønsted acid.

9. The process according to claim 1, wherein the furandicarboxylate containing polyester is part of a polymer composition further comprising one or more polymers selected from the group consisting of polyethyleneterephthalate, polyolefins, polyvinylchloride, polylactic acid, polyamides and mixtures thereof.

10. The process according to claim 9, wherein the polymer composition has been obtained from waste.

11. The process according to claim 1, wherein the alcohol comprises from 1 to 12 carbon atoms, the alcohol preferably being methanol, ethanol, ethylene glycol, 1,3-propane diol, 1,4-butadiol or a mixture thereof.

12. The process according to claim 1, wherein the reaction temperature ranges from room temperature to 350° C.

13. The process according to claim 1, wherein the process is performed in batch mode.

14. The process according to claim 1, wherein a stream containing the polymer composition is continuously fed into a reactor and a product stream containing furandicarboxylate compound and diol is continuously withdrawn from the reactor.

15. The process according to claim 14, wherein the process is conducted in a continuous stirred tank reactor.

16. The process according to claim 14, wherein furandicarboxylate compound is separated from the product stream.

17. The process according to claim 16, wherein at least part of the furandicarboxylate compound that has been separated from the product stream is used for the manufacture of poly(alkylene furandicarboxylate).

* * * * *